United States Patent [19]

Dorn et al.

[11] Patent Number: 5,539,141

[45] Date of Patent: Jul. 23, 1996

[54] MIXED BORIC ACID/PHOSPHORIC ACID ESTERS OF POLYOLS, THEIR PREPARATION AND USE

[75] Inventors: Karlheinz Dorn, Budenheim; Klaus Frankenfeld, Hunfelden; Hans-Dieter Nagerl, Dudenhofen; Sonja Schlarb, Ingelheim; Klaus Sommer, Bad Durkheim, all of Germany

[73] Assignee: Chemische Fabrik Budenheim Rudolf A. Oetker, Budenheim, Germany

[21] Appl. No.: 351,315

[22] PCT Filed: Jun. 14, 1993

[86] PCT No.: PCT/EP93/01497

§ 371 Date: Feb. 21, 1995

§ 102(e) Date: Feb. 21, 1995

[87] PCT Pub. No.: WO93/25560

PCT Pub. Date: Dec. 23, 1993

[30] Foreign Application Priority Data

Jun. 16, 1992 [DE] Germany ............................ 42 19 711.2

[51] Int. Cl.⁶ .................................................... C07F 9/09
[52] U.S. Cl. .................................................... 558/72
[58] Field of Search ................................................ 588/72

[56] References Cited

U.S. PATENT DOCUMENTS

| | | | |
|---|---|---|---|
| 3,031,280 | 4/1962 | Fay et al. | 558/72 X |
| 3,639,533 | 2/1972 | De Pierri, Jr. | 558/164 |
| 4,522,629 | 6/1985 | Horodysky et al. | 558/72 X |
| 4,536,306 | 8/1983 | Horodysky et al. | 558/72 X |
| 4,557,844 | 12/1985 | Horodysky | 252/49.9 |

*Primary Examiner*—Robert W. Ramsuer
*Assistant Examiner*—Michael G. Ambrose
*Attorney, Agent, or Firm*—Oblon, Spivak, McClelland, Maier, & Neustadt

[57] ABSTRACT

Described are mixed boric acid/phosphoric acid esters which may be obtained by subjecting at least one phosphorus compound capable of ester formation and at least one boron compound capable of ester formation simultaneously to an esterification reaction with at least one polyol and/or a derivative thereof capable of ester formation. Such esters may be prepared in an aqueous medium and find use in the flame-proofing treatment of a variety of materials, as acid catalysts for acid-curing synthetic materials, for controlling boron deficiencies in cultivated plants, and in many other fields of application.

27 Claims, No Drawings

MIXED BORIC ACID/PHOSPHORIC ACID ESTERS OF POLYOLS, THEIR PREPARATION AND USE

This application was filed under 35 U.S.C. §371 and was based upon PCT International Application No. PCT/EP93/01497, which was filed on Jun. 14, 1993.

The present invention relates to mixed boric acid/phosphoric acid esters of polyols as well as to preparation and use thereof.

Preparation of both boric acid esters and phosphoric acid esters has been known for a long time from e.g. standard publications on technical chemistry.

In Ullmann: Encyclopaedia der technischen Chemie, 4th Edition, Vol. 8, page 653, there is described e.g. the preparation of boric acid esters. According to this publication, the preparation starts directly from boric acid or boron trioxide and the respective alcohol. The water resulting from the reaction is removed by azeotropic distillation from the equilibrium reaction mixture. Used as water entrainers are benzene, toluene, xylene or an excess of primary aliphatic alcohols. The boric acid esters are used, for instance, as oxidation inhibitors in additives for oils and fuels, and as hydraulic and brake fluids. Boron-modified phenolic resins of phenyl borates and formaldehyde are used as binders for flame-resistant molded articles such as brake liners. Methyl and ethyl borates are used in the preparation of sodium boranate.

According to the state of the art, phosphoric acid esters are prepared on an industrial scale by reacting alcohols with phosphorylating agents such as phosphoryl chloride, phosphorus pentoxide or polyphosphoric acids. Described in U.S. Pat. No. 4,100,231 is the esterification of orthophosphoric acid with alcohols in the presence of considerable quantities of alkali hydroxide.

While the reaction of phosphoryl chloride with alcohols under appropriate conditions allows the production of mono-, di- and triesters of phosphoric acid, alcoholysis of phosphorus pentoxide always leads to a "sesqui-phosphate" which consists of a substantially equimolar mixtures of mono- and diesters of phosphoric acid together with minor amounts of condensed phosphoric acid esters. Polyphosphoric acids subjected to alcoholysis provide mixtures which consist predominantly of monoesters next to a small proportion of diesters. With orthophosphoric acid, there will normally be formed nothing but monoesters.

Phosphoric acid esters constitute a broad class of materials which find use in many applications, e.g. as surfactants in detergents and cleaning agents, as plasticizers in various synthetic materials, as plant protectants, as anti-corrosive agents, for metal extraction, and as flame-proofing agents.

It is the object of the invention to modify the known phosphoric acid esters in a manner improving their properties and widening their range of use. Moreover, their preparation method shall be improved, especially with respect to usable starting materials and the ease of controlling the esterification reaction.

According to the invention, the above object is achieved by mixed boric acid/phosphoric acid esters of polyols which are obtainable by subjecting at Least one phosphorus(V)-compound capable of ester formation and at least one boron compound capable of ester formation simultaneously (i.e. in a one-pot reaction) to an esterification reaction with at least one and/or one polyol derivative capable of ester formation under the given conditions.

Preferably, this esterification reaction is conducted under continuous removal of the side products formed during reaction and of the optionally used solvent. This applies particularly when (as in a specifically preferred embodiment of the present invention) water is formed as a side product during esterification and, respectively, water is additionally used as a solvent.

As boron compound capable of ester formation, there may be used any compound which is known to undergo under appropriate conditions an esterification reaction with alcohols and, respectively, with derivatives thereof which are principally capable of ester formation. Specific examples of such compounds are $B_2O_3$, boric acid ($H_3BO_3$), metaboric acid ($HBO_2$), as well as boron halides (e.g. $BF_3$, $BCl_3$ and $BBr_3$) and boric acid esters such as triethyl borate and trimethyl borate which are subject to transesterification on reaction with the (in comparison to monoalcohols, more reactive) polyols.

According to the invention, preferred boron compounds are $B_2O_3$ and boric acid, especially because of their availability and ease in handling. Boric acid is normally used in crystallized form.

As phosphorus compounds capable of ester formation, there may be used, just as in the case of boron compounds, all compounds of (pentavalent) phosphorus which are known to undergo an esterfication reaction on reaction with an alcohol and, respectively, a derivative thereof capable of ester formation (e.g. carboxylic acid ester). Specific examples of such compounds are $P_2O_5$, orthophosphoric acid and polyphosphoric acids, as well as halogenated compounds such as phosphoryl chloride ($POCl_3$) and $PCl_5$, phosphoric acid esters (particularly of monoalcohols) and the like. According to a specifically preferred embodiment of the present invention, there is used orthophosphoric acid, especially water-containing phosphoric acid obtained e.g. by a thermal process or through purification of wet-process phosphoric acid. Commercially available phosphoric acids of that type have $H_3PO_4$-concentrations of from 75 to 86% by weight.

The polyols to be used in accordance with the invention may be of an aliphatic, cycloaliphatic or aromatic nature and may have primary, secondary and/or tertiary hydroxyl groups. Preferred are aliphatic and cycloaliphatic polyols as, on use of aromatic polyols, there is occasionally observed a discoloration of the reaction products which may be undesired for specific applications. With respect to reactivity, there are preferably used polyols having (at least in part) primary and/or secondary hydroxyl groups. The carbon number of the polyols used in accordance with the invention is normally from 2 to 20, in particular from 2 to 6. The number of OH-groups in these polyols is preferably in the range of from 2 to 12 and, in particular, in a range of from 2 to 6. Also preferred is that the polyols used are capable of forming esters having a 5-membered and, in particular, a 6-membered ring. This applies to polyols that have hydroxy groups in 1,2-position and particularly in 1,3-position. The polyols used in accordance with the invention preferably have a molecular weight in the range of from 62 (ethylene glycol) to 182 (e.g. mannitol).

In addition to the (at least two) hydroxyl groups, the polyols used may have other functional groups, e.g. halogen (particularly Cl and F), alkoxy (particularly $C_1$–$C_4$ alkoxy such as ethoxy and methoxy), ether linkages in the backbone (e.g. polyalkylene glycol), and (preferably tertiary) amino groups. The polyols may also be used e.g. in form of compounds having protected hydroxyl groups (e.g. ester groups), or they may comprise such protected hydroxyl groups in addition to free hydroxyl groups. Via the ester groups, if they are not subject to considerable transesterificaction, there may be introduced further functional groups into the desired ester, which may later serve for other reactions of the boric acid/phosphoric acid esters of the invention. Thus, for instance, a (meth)acrylic acid residue may later serve for polymerization reactions with other olefinically unsaturated compounds, involving the carbon-carbon double bond.

Specific examples of polyols to be used in accordance with the invention are diols such as ethane diol, 1,2- and 1,3-propane diol, 1,2-, 1,3-, 1,4- and 2,3-butane diols, and pinacol; triols such as glycerol, trimethylol methane, -ethane and -propane; tetrols such as erythritol and pentaerythritol; pentols such as arabitol and xylitol; hexols such as mannitol and sorbitol; as well as di- and polypentaerythritols, inositols and aromatic polyols such as 1,4-dimethylolbenzene, 2,4-dimethylol-1,3-dihydroxybenzene, dihydroxybenzenes (particularly pyrocatechol) and trihydroxybenzenes.

Polyols preferred in accordance with the invention are ethane diol, trimethylol propane, pentaerythritol and mannitol.

Specific polyols having other functional groups are e.g. monoethanol amine, diethanol amine and triethanol amine, diethylene glycol and dipropylene glycol as well as 3-chloro-1,2-propane diol. As ester compounds, there may be used e.g. esters of (meth)acrylic acid, formic acid, acetic acid and propionic acid.

The polyols useful in accordance with the invention are not limited to monomeric compounds; polymeric compounds may be used as well, e.g. polyvinyl alcohol and, respectively, (partially) saponified polyvinyl acetate or polyalkylene glycols of a high condensation degree. Such compounds are preferably used in admixture with monomeric polyols, but even on sole use of monomeric polyols, the use of mixtures thereof may be advantageous for certain applications of the respective final products. Finally, the polyols may, if desired, also be used in mixture with monoalcohols such as methanol and ethanol. Such monoalcohols anyway constitute side products of the reaction when one or more of the respective boron and phosphorus starting materials are used in form of an ester with such an alcohol. A monoalcohol may be used e.g. for modification of the mixed esters according to the invention (when working with polyol quantities which do not suffice for esterifying all of the available esterifiable acid groups) or as entrainers for the water formed during esterification (azeotrope formation).

In general, boron compounds and phosphorus compounds are used in such quantitative ratios that the atomic ratio B/P lies in a range of from 5/95 to 95/5. Preferred is an atomic ratio of from 9/1 to 1/9, and particularly preferred is a range of from 7/3 to 3/7. For a multitude of applications, a B/P-ratio of about 1/1 (e.g. of from 1.5/1 to 1/1.5) proved to be particularly favorable.

In the reaction of the starting materials in an aquous medium which, according to the invention, is particularly preferred and discussed below in detail, the esterification degree of the acid component may be influenced by the B/P-ratio. Thus, using various polyols having molecular weights between 62 and 182 and OH-group numbers of from 2 to 6, tests were conducted with different B/P-ratios of the respective starting materials. The molar ratio of acid (phosphoric acid+boric acid)/polyol was 1/1 in every test. As mean value from all of these tests, the following results were obtained:

| B/P-ratio | 0.5/1.0 | 1.0/1.0 | 2.0/1.0 |
|---|---|---|---|
| average of esterified acid-OH-groups per acid molecule | 1.11 | 1.45 | 2.00 |

The above results show that there exists a linear relation between the B/P-ratio in the starting materials and the esterification degree of the acid. At a B/P-ratio of 0.5/1.0, there are formed (on the average) predominantly acid monoesters with a minor proportion of acid diesters while, at a B/P-ratio of 1/1, the proportions of monoester and diester are almost equal. At a B/P-ratio of 2/1, there are formed (on the average) only acid diesters. Thus, there exists the possibility of influencing the esterification degree of the resulting acids by means of the B/P-ratio.

Even the ratio of acid used to polyol (alcohol) used shows the expected effect on the chemical nature of the resulting final products. In accordance with the invention, it is preferred to select the molar ratio of polyol to the total of present (menemetic) boron and phosphorus compounds not higher than 3/1 (at least in cases where reaction is not to be conducted in an excess of polyol as solvent). Particularly preferred is a molar ratio of polyol to boron plus phosphorus compounds of not more than 2/1. Also preferred is the use of at least two and, in particular, at least three molar equivalents of polyol per mole of phosphorus compound plus boron compound. (All of the above ratios apply to cases were exclusively polyol, i.e. no additional monoalcohol, is used.)

In the normal case, there is chosen a molar ratio of acid to polyol of about 1/1 (e.g. 1.5/1 to 1/1.5) so that essentially mixtures of mono- and diesters are obtained. If esters comprising a high proportion of polyol triesters are to be prepared (which evidently is possible only by using polyols having at least three hydroxyl groups), the acid/polyol ratio must be shifted towards more acid. In reverse, when esters having weakly acidic characteristics are to be prepared, it is more favorable to shift the acid/polyol ratio towards more alcohol. The best results are obtained as a rule with a molar ratio of acid to alcohol in a range of from 2/1 to 1/2.

Using various polyols having molecular weights in the range of from 62 to 182 and OH-group numbers of from 2 to 6 as well as a B/P-ratio in the starting materials of 1/1, there were tested esterification reactions in an aqueous medium wherein the molar ratio of acid/polyol varied in the range of from 1.0/2.0 to 2.0/1.0. From the results thus obtained, there were calculated the esterified groups based on both the acid molecule and the polyol molecule. The following mean values were thus found:

| Acid/polyol molar ratio | 1.0/2.0 | 1.0/1.0 | 2.0/1.0 |
|---|---|---|---|
| esterified hydroxyl groups per polyol molecule | 0.68 | 1.36 | 2.67 |
| esterified groups per acid molecule | 1.37 | 1.36 | 1.33 |

The above results prove that the esterification degree of the polyol at a constant B/P-ratio depends in linear form on the molar ratio of acid/polyol.

According to the invention, the reaction of boron compound and phosphorus compound with polyol need not necessarily take place with all reactants being already present at the start of the reaction and in the total amounts to be used. In certain cases, it may be convenient to first react only the Boron compound(s) with the polyol component and then .add the phosphorus compound(s) as well as optionally further polyol. In a like manner, one may first react boron as well as phosphorus compounds with a certain polyol and subsequently add to the reaction mixture one or more polyols that differ from the originally added polyol.

If necessary, there may also be added to the reaction mixture conventional esterification catalysts though this will not be required in most cases.

The reaction temperature depends on the reactivity of the starting materials used. While with very reactive starting materials such as boron- and phosphorus-halogen compounds, cooling may even be required, working at room temperature and particularly at slightly raised temperature is preferred on use of boric acid and phosphoric acid (in an aqueous medium). Particularly preferred temperature ranges are between 50° and 150° C., especially between 90° and 130° C. (e.g. from 95° to 125° C.). The maximum temperature to be used is determined, among others, by the volatility and decomposition temperature of the respective starting materials (especially the polyol) and, respectively, the desired ester.

On various formulations which differed with respect to polyol specification as well as in B/P-ratio, there were conducted esterification reactions in an aqueous medium at a heating bath temperature of from 98° to 120° C. under comparable conditions. It was found that in all cases a higher esterification degree was obtained at higher temperature. On the average, the increase amounted to 24%.

The boric acid/phosphoric acid esters of the invention preferably have a boron and phosphorus content within the below limits:

Boron (calculated as $B_2O_3$)—1.4 to 25.0% by weight
Phosphorus (calculated as $P_2O_5$)—3.2 to 44.0% by weight.

Preferably, the organic residues derived from the used polyols (alcohols) constitute from 48.0 to 83.0% by weight of the boric acid/phosphoric acid esters of the invention.

On working in an aqueous medium, the mixed boric acid/phosphoric acid esters are normally obtained in form of viscous solutions. When cooled down to room temperature, they solidify and —depending on their composition—form highly viscous, paste-like or solid masses. The color of the esters extends from fully transparent over opaque to white. As a rule, they are odorless and non-hygroscopic. They show intumescent characteristics, i.e. they expand when heated and form firm structures on decomposition. Moreover, the boric acid/phosphoric acid esters of the invention are, as a rule, water-soluble and form colorless solutions of an acidic pH which, depending on the composition of the esters, may be from 1.8 to 2.5 in 1% solutions.

Due to the acidic characteristics, there may be prepared salts from the boric acid/phosphoric acid esters of the invention. Preparation of these salts preferably takes place in an aqueous solution and at ester concentrations of from 1 to 80% by weight, preferably from 5 to 30% by weight. The amount of cations required for salt formation may be determined in advance by e.g. titration of the ester with a standardized sodium hydroxide solution. Preferably used for salt formation are alkali metals (especially sodium and potassium), alkaline earth metals (especially magnesium) and (organic) nitrogen compounds. They may reacted, e.g. in form of the free bases or as carbonate salts, in the caculated amounts with the aqueous ester solutions. Particularly suited as organic nitrogen compounds are di- and polyamines such as ethylen diamine, diethylene triamine, hexamethylene tetramine, melamine and guanidine. On salt formation with the two last mentioned amines, there will be obtained salts of poor solubility. These may be filtered and dried in the usual manner, and rewashing of the filter cake is not required.

According to a particularly preferred embodiment of the present invention, the boric acid/phosphoric acid esters are prepared in an aqueous medium even though one may use any solvent that does not react with the starting materials used and, respectively, does not interfer with the esterification reaction. Examples of such solvents are monoalcohols (e.g. methanol, ethanol, propanol), esters, ethers, ketones, aromatic compounds such as toluene and xylenes, and the like. As already mentioned above, even an excess of polyol may be used as solvent.

The known methods of preparing boric acid esters and phosphoric acid esters avoid the presence of water in the esterification reaction. Thus, only non-aqueous substances are used as starting materials, the anions being esterified in form of their anhydrides or as condensed acids.

It was therefore extremely surprising that, according to the invention, the mixed boric acid/phosphoric acid esters of polyols could successfully be prepared from aqueous solutions. Moreover, preparation from aqueous solutions is of considerable advantage in that the starting materials may be phosphorus and boron compounds such as aqueous phosphoric acid and boric acid, which are prepared on an industrial scale and, thus, have a very favorable price. Furthermore, as compared to prior art methods, the esterification reaction in an aqueous medium can be conducted without involved, complex and time-consuming process controlling measures. All starting materials required for formation of the mixed ester may already be dissolved (or even only dispersed) in the aqueous starting solution. Side reactions or decomposition reactions which, due to faults in quantitative proportioning, are quite possible in conventional methods of preparing phosphoric acid esters cannot occur here. The composition of the product will be determined definitely by the formulation of the starting solution.

As compared to the preparation of pure phosphoric acid esters, the esterification reaction in the present case proceeds at a surprising speed which possibly might be attributed to a catalytic effect produced by the equally present boric acid compound.

When working in an aqueous medium, one may e.g. dissolve the starting materials in the process water (optionally under heating) and react them as a homogeneous aqueous starting solution either batch-wise or continuously in a vacuum evaporator. Advantageous is the use of a thin-film vaporizer. During reaction, the added process water as well as the reaction water released during ester formation will evaporate, the reaction being completed when no more water is separated from the reactants. The vaporized water may be condensed so as to determine the esterification degree from the quantitative balance of the water. Moreover, the drawn-off water may again be used as process water.

The reaction water serves as a solvent and contributes in the preparation of the aqueous starting solution for the production of the ester according to the invention. The starting solution may comprise in dissolved form all of the respective reactants in the required amounts.

The required amount of water (when working in a solution) is determined by the water solubility of the individual components, the water content of the optionally (and preferably) used orthophosphoric acid and—especially on use of a mixture of various polyols—by how the solubilities of the respective polyols mutually influence each other. The water requirements may be minimized when the preparation of the aqueous starting solution is conducted in a temperature range of from 50° to 90° C., preferably at 60° to 80° C.

Thus, the water content of the aqueous starting solution generally varies over a range of from 15 to 55% by weight, particularly between 20 and 40% by weight. As a rule, a water content of the aqueous starting solution of from 30 to 40% by weight is especially advantageous.

Esterification of the aqueous medium is preferably accomplished by evaporating the water from thin liquid films of the starting solution. Used for this purpose may be e.g. a vacuum thin-film vaporizer operating preferably within a temperature range of from 95° to 125° C. (temperature of the heating medium) and at a pressure of 20 to 60 mbar. When the ester is prepared by batch-type operation, e.g. in a rotary evaporator, a dwelling time of 60 to 80 minutes will be sufficient under the above described conditions to achieve an esterification equilibrium. However, as time-dependent check and control of the process has been eliminated, production of the boric acid/phosphoric acid esters of the invention is no longer subject to batch-type operation. Thus, the esters of the invention may also be prepared in a continuous process.

What quantities of boric acid/phosphoric acid ester may be produced per unit of time depends on various parameters. Of specific importance among these parameters is the amount of water evaporated from the aqueous starting solution as well as the operational efficiency of the vacuum evaporator which, in turn, is a result of pressure and temperature adjustment. Under the above preparation conditions, it is possible to continuously produce ester in an amount of from 30 to 70 kg per hour on an evaporator area of 1 m$^2$.

Besides the thin-film vaporizers of the rotary or falling-film evaporator type, there are specifically suited for preparing in accordance with the invention the present esters all evaporation reactors which are capable of forming a constantly restored liquid film under the stated pressure and temperature conditions.

Due to the variables present in the system of boric acid/phosphoric acid esters, there may be recovered by the same production process a multitude of different mixed ester types which are suited for a large variety of applications. This multitude of possible mixed boric acid/phosphoric acid esters opens for this group of compounds a very wide range of applications, some of which shall be described below by way of example. In all cases, the esters may be used either as such or in form of a salt and/or mixed with synthetic materials and polymers.

A broad field of use for the esters of the invention resides in flame-proofing paper, paper products, corrugated cardboard, wood (e.g. fiberboard, chipboard or the like), textile materials, synthetic materials, building materials and other combustible material. The esters of the invention are ideally suited for this purpose and provide better results than the materials hitherto used.

The esters of the invention, especially those having a relatively high P-content, are particularly suited for a flame-retarding treatment of combustible materials (fire protection). Besides, these esters comprise a B-component. In the case of fire, this prevents smoldering (especially of cellulose materials) and suppresses the development of smoke gases. The organic portion of the esters of the invention is derived from the polyols used and, in the case of fire, leads to intumescent surface layers that limit the propagation of flames. As the inorganic components (B,P) of the esters according to the invention are associated with a large organic residue, these inorganic components may be incorporated without problems into organic polymers. In case of fire, the P- and B-components of the esters react with each other to form an insoluble solid boron phosphate, thus providing a positive contribution to environment protection.

As to the flame-proofing of different combustible materials with flame-retarding substances, there cannot be made any generally applicable statements as each specific application requires some other technique and the interactions between combustible material and flame-retarding substance must also be considered. Thus, there shall be described below in detail some specific cases for the purpose of illustration.

For the flame-proofing of paper and paper products, the esters of the invention are preferably used in form of aqueous solutions. Particularly preferred is that these aqueous solutions additionally comprise dispersed acrylate which is especially advantageous for the flame-proofing of corrugated cardboard. Moreover, in the flame-proofing of paper, paper products and corrugated cardboard, there are preferably used boric acid/phosphoric acid esters wherein an average of 1.0 to 1.5 OH-groups per molecule of polyol is esterified. For the preparation of such esters, there are preferably used polyols that have an OH-group content of at least about 40% by weight, preferably of at least about 45% by weight.

Flame-proofing of paper, paper products, and corrugated cardboard may take place e.g. by immersion or by spraying the paper, paper product or corrugated cardboard with the aqueous solution and subsequently drying it. Esters of a suitable type are preferably applied in such an amount that the treated and dried material shows a $B_2O_3$-content of from 1.6 to 2.4% by weight and a $P_2O_5$-content of from 5.5 to 8.5% by weight.

The mixed boric-acid/phosphoric acid esters of the invention, especially in mixture with aqueous polyvinyl acetate dispersions, are also suited for the flame-proofing of carpets and other heavy textiles. For this purpose, there may be applied e.g. a mixture of an about 50% aqueous polyvinylacetate dispersion and the undiluted boric acid/phosphoric acid ester to the back side of the carpet and dried thereon. Optionally, as other additives inorganic materials such as aluminum hydroxide may be worked into the above mixture. The carpets subjected to the above flame-proofing treatment preferably have a $B_2O_3$-content of from 1.6 to 2.7% by weight and a $P_2O_5$-content of from 5.9 to 9.5% by weight.

For the flame-proofing of textile materials, the esters of the invention are preferably also used in form of aqueous solutions. Those aqueous solutions additionally containing prepolymer are particularly preferred. Preferred are prepolymers based on acrylates and prepolymers containing basic nitrogen groups.

For the flame-proofing of textile materials, there are particularly suited those esters of the invention wherein an average of from 1.0 to 2.0 and especially from 1.0 to 1.7 OH-groups per molecule of polyol are esterified. Moreover, for preparing esters of the invention which are particularly suited for the flame-proofing of textiles, there are preferably used polyols having an OH-group content of about 50% by weight (e.g. from 45 to 55% by weight).

As in the flame-proofing treatment of paper and the like, flame-proofing of textiles may also be accomplished by e.g. immersion or spraying of the textiles and subsequent drying. The thus treated textiles preferably have a $B_2O_3$-content of 1.1 to 3.4% by weight and $P_2O_5$content of 2.3 to 6.9% by weight.

The boric acid/phosphoric acid esters of the invention also find use in the preparation of flame-retarding paints or coatings required for the large-area flame-proofing of building, steel constructions or individual structural parts. Here too, above described properties of the esters will be effective. They may be added e.g. to prepolymers and then applied to the structural elements to be protected. On curing of the protective layers, there will occur chemical reactions between ester and prepolymer.

The mixed boric acid/phosphoric acid esters of the invention are also suited (especially in form of their salts) for the flame-proofing of synthetic materials such as polyamides, polyolefines, e.g. polyethylene, polypropylene and the like. Melamine salts proved to be particularly useful for this purpose. These melamine salts are thermally very stable compounds, the decomposition temperatures of which are in the range of from 270° to 320° C. Thus, they may be worked without decomposition into the molten synthetic materials, e.g. by means of an extruder. The melamine salts of the esters according to the invention are, as a rule, very finely divided flaky compounds showing a nacreous luster. As they have no abrasive characteristics, they have no damaging effect on the extruder tools during processing. Moreover, their water solubility is very low. In an 10% aqueous suspension of the melamine salts, conductivity will be increased only by 170 to 250 µS. This characteristic prevents the flame-proofing component from subsequently bleeding out of the synthetic material and, thus, from reducing the electric resistance of the correspondingly treated synthetic materials.

Fleece materials bonded by phenolic resins and intended for sound absorption are prepared from short torn fibers, glass fibers, polyacrylic fibers and phenolic resins (novolak resins). As cured molded elements, they are used in the automotive industry and in household appliances. The products thus prepared must meet the standard specifications of DIN 54333 and DIN 75200 with respect to combustion behavior. Some consumers even demand increased fire protection corresponding to the Volvo Fire Test STD 1027, 5188.

It was found that by admixing the boric acid/phosphoric acid esters of the invention (e.g. in form of their melamine salts) to phenolic resins, increased fire protection according to the Volvo standard will be achieved. The melamine salt content of the phenolic resin sufficient for this purpose varies, as a rule, over a range of from 15 to 35% by weight. Insulating fleece materials treated with the esters of the invention preferably have a $B_2O_3$-content of from 0.8 to 1.8% by weight, a $P_2O_5$-content of from 2.2 to 3.2% by weight and an N-content of from 2.0 to 8.0% by weight.

A further wide field of application is opened for the boric acid/phosphoric acid esters of the invention by their acid properties in conjunction with a large organic residue. The esters of the invention are, in particular, acids of medium strength with inorganic and organic functional groups. Thus, they are suited as acid catalysts in the processing of synthetic materials, specifically in the processing of acid-curing synthetic materials, to control the setting process. In contrast to conventional curing agents which usually are strong inorganic acids leading to rapid uncontrollable setting, use of the esters of the invention permits any desired extension of the setting time. Such, an extension is necessary when curing of the synthetic material is accompanied by a slowly proceeding molding process. When the esters of the invention are used as curing catalysts, the synthetic materials will simultaneously be subjected to a flame-proofing treatment.

As acid-curing-synthetic materials, there may be mentioned in first place phenol formaldehyd resins (resols). The esters of the invention are incorporated in such resin compositions preferably in amounts resulting in a $P_2O_5$-concentration in the range of from 1.0 to 4.0% by weight, particularly in a range of from 1.5 to 3.5% by weight.

As acid catalysts for the above described application, there are specifically suited such boric acid/phosphoric acid esters that consist of mixtures of mono- and diesters with a diester portion of from 10 to 60% by weight. Preferably, the polyols and, respectively, polyol mixtures used for preparing such esters have an average of 2 to 4 OH-groups, particularly 2.5 to 3.25 OH-groups per molecule.

It was also found that the esters of the invention are suited for precisely controlling the foaming of phenol formaldehyde resins in the course of the curing process. This applies especially to resins which still comprise a certain excess of free formaldehyde or of other easily volatile substances. With such resin mixtures, strong expansion of the reaction mixture takes place on curing. After curing, the resin is in form of a solid foam with closed hollow spaces (cells). The weight per unit of volume of the cured phenol formaldehyde resins is reduced from an average of 1.19 kg/l for unfoamed samples to values of from 0.4 to 0.7 kg/l for the foamed samples. This leads to a volume increase of 170 to 300%.

It has now been found that the change in volume and, respectively, weight per unit of volume depends on the type of mixed boric acid/phosphoric acid ester used as curing agent. Thus, the boric acid/phosphoric acid esters of the invention are suited for controlling the foaming process of e.g. phenol formaldehyde resins.

Curing as well as foaming of the phenol formaldehyd resins with the esters of the invention is preferably conducted at about 40° C.

A further field of application for the esters of the invention is found in plant protection for controlling acute boron deficiencies. Preferably used for this purpose are the potassium and/or ammonium salts of the esters according to the invention.

Boric acid functions as a micro-nutrient, especially for sugar beets. In case of boron deficiencies, heart rot and dry rot will occur. The boron requirement is normally satisfied by boron-containing fertilizers. However, interactions between the soluble boron compounds and the calcium ions will take place in the soil, and this will cause fixation of the boron within the soil. Thus, it may come to boron deficiency phenomena which, especially in the case of sugar beet cultivation, may result in considerably reduced crops.

It was found that the boric acid/phosphoric acid esters of the invention, particularly in form of their potassium and/or ammonium salts, may be used for controlling these acutely occurring boon deficiencies. For this purpose, they may be applied e.g. as a sort of top-dressing in form of an 0.2 to 0.5% spraying solution. The plants will take up the boron not through the roots but directly over the affected leaves, and the boron wall become immediately effective as the boric acid component is present in organically bound form. The requirement of ester according to the invention depends on the intensity of the boron deficiency. Normally it will be in the range of from 10 to 20 kg of ester per hectare.

The following examples and use examples illustrate the invention without limiting its scope. Unless otherwise stated, all parts and percentages are related to weight.

EXAMPLE 1

Into a 1,500 ml round-bottom flask were weighed:

| | | |
|---|---|---|
| Boric acid $H_3BO_3$ | (100%) | 58.8 g = 0.951 mole |
| Phosphoric acid $H_3PO_4$ | (86.2%) | 108.1 g = 0.951 mole |
| Trimethylol propane | (100%) | 255.2 g = 1.902 mole |

-continued

| | |
|---|---|
| H₂O | 264.0 g |
| Total formulation | 686.1 g |

The resulting mixture was heated to 75° C. until a clear solution was obtained. The round-bottom flask was then connected to a vacuum rotary evaporator, and water was distilled off under a vacuum. The pressure was slowly (within 20 minutes) reduced to 29 mbar. It was observed after 65 minutes that water no longer distilled off. The flask remained connected to the rotary evaporator for a total of 120 minutes. Bath temperature was 98° C. The flask was then removed from the rotary evaporator, dried and weighed. The reaction residue was determined to be 355.4 g. The esterification degree (ester number) is calculated from the molar number of the reaction water divided by the molar number of the polyol used.

Calculation:

| | |
|---|---|
| Total formulation | 686.1 g |
| Reaction residue | −355.2 g |
| Total H₂O loss | 330.9 g |
| H₂O addition in formulation | 264.0 g |
| H₂O amount from phosphoric acid | 14.9 g |
| H₂O amount in formulation | −278.9 g |
| Total H₂O loss | 330.9 g |
| H₂O amount in formulation | −278.9 g |
| Reaction water | 52.0 g = 2.891 mole |

Ester number $\frac{2.891}{1.902} = 1.52$

Thus, an average of 1.52 OH-groups of the polyol were esterified in the reaction.

The product is a flowable, clear, paste-like mass of a slightly yellowish color, having a $B_2O_3$-content of 9.3% and a $P_2O_5$-content of 19.3%.

EXAMPLE 2

As described in Example 1, the following starting mixture was subjected to an esterification reaction in a 750 ml flask:

| | | |
|---|---|---|
| Boric acid H₃BO₃ | (100%) | 39.2 g = 0.634 mole |
| Phosphoric acid H₃PO₄ | (86.4%) | 36.0 g = 0.317 mole |
| Glycerol | (96.0%) | 91.2 g = 0.951 mole |
| H₂O | | 117.4 g |
| Total formulation | | 283.8 g |
| Pressure | 61 mbar | |
| Time | 120 min | |
| Bath temperature | 98° C. | |
| Reaction residue | 128.4 g | |
| Calculation of the ester number | | |
| Total formulation | | 283.8 g |
| Reaction residue | | −128.4 g |
| Total H₂O loss | | 155.4 g |
| H₂O addition | | 117.4 g |
| H₂O amount from H₃PO₄ | | 5.0 g |
| H₂O amount from glycerol | | 3.6 g |
| H₂O amount in formulation | | 126.0 g |

| | |
|---|---|
| Total H₂O loss | 159.4 g |
| H₂O amount in formulation | −126.0 g |
| Reaction water | 33.4 g — 1.856 mole |

Ester number $\frac{1.856}{0.951} = 1.95$

B- and P-content of the reaction product
17.9% by weight of $B_2O_3$
18.2% by weight of $P_2O_5$
A flowable opaque paste, solid after cooling.

EXAMPLE 3

As described in Example 1, the following formulation is reacted in a 750 ml flask:

| | | |
|---|---|---|
| Boric acid H₃BO₃ | (100%) = | 14.7 g = 0.238 mole |
| Phosphoric acid H₃PO₄ | (86.2%) = | 27.1 g = 0.238 mole |
| Mannitol | (100%) = | 173.1 g = 0.951 mole |
| H₂O = | | 180.0 g |
| Total formulation = | | 394.9 g |
| Pressure | 69 mbar | |
| Time | 120 min | |
| Temperature | 98° C. | |
| Reaction residue | 200.1 g | |
| Total formulation | | 394.9 g |
| Reaction residue | | −200.1 g |
| Total H₂O loss | | 194.8 g |
| H₂O addition | | 180.0 g |
| H₂O amount from phosphoric acid | | 3.7 g |
| Total H₂O in formulation | | 183.7 g |
| H₂O loss | | 194.8 g |
| Total H₂O amount | | −183.7 g |
| Reaction water | | 11.1 g = 0.617 mole |

Ester number: $\frac{0.617}{0.951} = 0.65$

B- and P-content of the reaction product:
4.1% by weight of $B_2O_3$
8.4% by weight of $P_2O_5$
The product is a solid white mass.

EXAMPLE 4

As described in Example 1, the following formulation is subjected to an esterification reaction in a 750 ml flask:

| | | |
|---|---|---|
| Boric acid H₃BO₃ | (100%) | 29.35 g = 0.475 mole |
| Phosphoric acid H₃PO₄ | (86.2%) | 54.12 g = 0.475 mole |
| Mannitol | | 86.53 g = 0.475 mole |
| H₂O | | 62.55 g |
| Total formulation | | 232.55 g |
| Pressure | 53 mbar | |
| Time | 140 min | |
| Bath temperature | 98° C. | |
| Reaction residue | 145.30 g | |
| Calculation of the ester number: | | |
| Total formulation | | 232.55 g |

-continued

| Reaction residue | −145.30 g |
| --- | --- |
| Total H$_2$O loss | 87.25 g |
| H$_2$O addition | 62.55 g |
| H$_2$O amount from H$_3$PO$_4$ | 7.47 g |
| H$_2$O amount in formulation | 70.02 g |
| Total H$_2$O loss | 87.25 g |
| H$_2$O amount in formulation | −70.02 g |
| Reaction water | 17.23 g = 0.957 mole |

Ester number: $\frac{0.957}{0.475} = 2.015$

B- and P-content of the reaction product:
11.4% by weight of B$_2$O$_3$
23.3% by weight of P$_2$O$_5$
The product is a solid, clear, glass-like mass.

EXAMPLE 5

As described in Examples 1 and 4, the starting formulation from Example 4 was subjected to an esterification reaction; however, in modification of Examples 1 and 4, the bath temperature was raised to 125° C.

| Pressure | 35 mbar |
| --- | --- |
| Time | 120 min |
| Bath temperature | 125° C. |
| Reaction residue | 140.99 g |
| Calculation of the ester number: | |
| Total-formulation | 232.55 g |
| reaction residue | −140.99 g |
| Total H$_2$O loss | 91.56 g |
| H$_2$O addition | 62.55 g |
| H$_2$O amount from H$_3$PO$_4$ | 7.47 g |
| H$_2$O amount in formulation | 70.02 g |
| Total H$_2$O loss | 91.56 g |
| H$_2$O amount in formulation | −70.02 g |
| Reaction water | 21.54 g = 1.197 mole |

Ester number: $\frac{1.197}{0.475} = 2.519$

The product is a solid, slightly opaque, glass-like mass.

EXAMPLE 6

Into a 750 ml round-bottom flask, there were weighed:

| Boric acid H$_3$BO$_3$ | (100%) | 19.52 g = 0.317 mole |
| --- | --- | --- |
| Phosphoric acid H$_3$PO$_4$ | (86.2%) | 72.08 g = 0.635 mole |
| Ethane diol | (98%) | 60.16 g = 0.951 mole |
| H$_2$O | | 130.00 g |
| Total formulation | | 281.76 g |

The round bottom flask was equipped with a fast running anchor agitator and weighed out. The flask was then connected with the stirrer still-in place to a vacuum distillation apparatus and the water was removed from the reaction mixture under strong agitation. Pressure was slowloy (within 35 minutes) reduced to 57 mbar. Heating bath temperature was 105° C. After a total running time of 185 minutes, further distillation of water could not longer be observed.

The round bottom flask with agitator was again weighed. The reaction residue was determined to be 120.78 g.

| Calculation of the ester number: | |
| --- | --- |
| Total formulation | 281.76 g |
| Reaction residue | −120.78 g |
| Total H$_2$O loss | 160.98 g |
| H$_2$O addition in formulation | 130.00 g |
| H$_2$O amount from phosphoric acid | 9.95 g |
| H$_2$O amount from ethane diol | 1.20 g |
| H$_2$O amount in formulation | 141.15 g |
| Total H$_2$O loss | 160.98 g |
| H$_2$O amount in formulation | −141.15 g |
| Reaction water | 19.83 g = 1.102 mole |

Ester number: $\frac{1.102}{0.951} = 1.16$

B- and P-content of the reaction product:
9.1% by weight of B$_2$O$_3$
37.3% by weight of P$_2$O$_5$
Flowable opaque mass, paste-like after cooling.

USE EXAMPLE 1

The flame-retarding properties of the boric acid/phosphoric acid esters of the invention were tested on filter papers. For this purpose, filter papers of the type "Schleicher-Schüll 597" were soaked with a 10% aqueous solution of an ester and subsequently dried whereupon ester absorption was determined by weighing; the filter papers were then treated for 15 seconds with a gas flame. Ester absorption of the filter papers was, on an average, 22.2% by weight (±15% rel.).

A positive valuation received the samples where ignition of the tested papers could not be accomplished. Particularly useful to this end are esters and mixtures thereof which comprise an average of about 1.3 esterified OH-groups per polyol molecule present in the ester. At the same time, the mean molecular weight of these polyols should be about 85, and they should have an average of 2 to 3 OH-groups.

It was found in the above test that, on the average, a P$_2$O$_5$-content of about 7.0% by weight and a B$_2$O$_3$-content of about 2.0% be weight, each based upon the amount of paper, will already be sufficient to prevent combustion of the tested papers. This means meeting the standards of fire safety class B3 according to DIN 4102/Part 1.

USE EXAMPLE 2

The test described in Use Example 1 was repeated with cotton fabrics. Samples of cotton fabrics (90 by 190 mm) were immersed for 5 minutes in a 10% aqueous polyethylene imine solution. The temperature of the solution was 80° to 90° C. The samples were then squeezed out and dried for about 15 minutes in a drying chamber at 100° C. They were then immersed for 5 minutes in a 10% aqueous solution of the esters according to the invention, squeezed out and dried again. The amount of flame-retarding agent (ester) absorbed by the cotton samples was determined by the weight before and after application. Combustion behavior was tested in a fire box according to DIN 50050. Here, the textile samples were flame-treated for 15 seconds in the testing device. In this test, the tip of the flame may not reach the index mark of 150 mm before 20 seconds have expired. Samples meeting the above requirement correspond to fire safety class B3 according to DIN 4102.

The following results were obtained:

Ester absorption of the cotton fabrics was, on the average, 22.8% by weight (±16% rel.). Particularly advantageous results provided esters or mixtures thereof wherein an average of about 1.5 OH-groups were esterified per polyol molecule present in the ester. Moreover, the respective esters preferably have about equal mono- and diester portions (based upon the acid). The polyols used for the preparation of these esters are preferably those with a mean molecular weight of about 110 which have an average of about 3.5 OH-groups.

In the above experimental tests, it was found that, on the average, a $P_2O_5$-content of about 5.7% and a $B_2O_3$-content of about 2.9%, each based on the cotton fabric, will be sufficient to meet the requirements of fire safety class B3 according to DIN 4102.

USE EXAMPLE 3

Samples of carpets were subjected to a flame-proofing treatment with aqueous solutions of the esters of the invention and then tested on their combustion behavior according to the specifications of DIN 54333. It was found that, on the average, a $P_2O_5$-content of about 7.7% by weight and a $B_2O_3$-content of about 2.1% by weight, each based upon the untreated carpet sample, will suffice to limit, on the average, the flame propagation rate $V_B$ to 19 mm/min. Subsequent smoldering of the carpet samples was not observed.

USE EXAMPLE 4

With acid-curing phenol/formaldehyde resins (resol type) as an example, there was tested the effect of mixed boric acid/phosphoric acid esters on the progress of the curing process of these resins.

In an open beaker were intensively mixed 100 g each of a phenol/formaldehyde resin with various amounts of differently composed boric acid/phosphoric acid esters. The boric acid/phosphoric acid esters were used in form of an aqueous solution consisting of 75% by weight of ester, 5% by weight of toluene sulfonic acid and 20% by weight of water. Determined was the period of time between ester addition and the onset of rosin curing (pot life). The tests were conducted in a drying chamber at a constant temperature of 40° C.

It was found in the above tests that the pot life of the resin/ester mixture is inversely proportional to the $P_2O_5$-concentration originating from the used ester. As mean values from three tests each, the following relationships were found:

| $P_2O_5$ - content of the resin (%) | | | | | | | |
|---|---|---|---|---|---|---|---|
| 3.55 | 3.30 | 2.83 | 2.65 | 2.50 | 2.45 | 2.00 | 1.54 |
| | | | Pot life (min) | | | | |
| 5.0 | 7.1 | 10.8 | 12.3 | 17.7 | 18.0 | 21.6 | 25.0 |

The above results show that a decrease in $P_2O_5$-content of a resin is accompanied by a linear increase in the pot life of that resin.

USE EXAMPLE 5

A phenol/formaldehyde resin having a free formaldehyde content of 2.5% by weight was cured and foamed. The test was conducted under the conditions described in Use Example 4. The change in weight per unit of volume was determined by weighing the foamed samples and determining their volume in liters.

The results thus obtained are summarized below as mean values from four tests each.

| Weight per unit volume of resin | $P_2O_5$ - and $B_3O_3$ - content in resin (%) | | | Ester number of boric acid/ phosphoric acid |
|---|---|---|---|---|
| (kg/l) | $P_2O_5$ | $B_2O_3$ | Sum | ester |
| 0.436 | 1.90 | 0.77 | 2.67 | 1.60 |
| 0.541 | 2.07 | 0.94 | 3.01 | 1.45 |
| 0.573 | 2.32 | 0.69 | 3.01 | 1.33 |
| 0.673 | 2.57 | 0.63 | 3.20 | 1.11 |

The above table shows that besides the concentration of $P_2O_5$ and $B_2O_3$ in the resin, the specification of the mixed boric acid/phosphoric acid ester, in particular the ester number, is decisive for the weight per unit of volume of the foamed phenol/formaldehyd resin. Thus, the foaming process can be controlled through the ester specification.

We claim:

1. A process for preparing boric acid/phosphoric acid esters of polyols, characterized by subjecting at least one phosphorus compound capable of ester formation and at least one boron compound capable of ester formation simultaneously to an esterification reaction with at least one polyol and/or a derivative thereof capable of ester formation.

2. The process according to claim 1, characterized in that the esterification reaction is conducted under continuous removal of the side products formed during reaction and of an optionally used solvent.

3. The process according to claim 1, characterized in that the phosphorus compound capable of ester formation is selected from $P_2O_5$, phosphoric acid, polyphosphoric acids and mixtures of said compounds.

4. The process according to claim 1, characterized in that the boron compound capable of ester formation is selected from $B_2O_3$, boric acid, metaboric acid and mixtures of said compounds.

5. The process according to claim 1, characterized in that the polyol is selected from compounds having 2 to 12 OH-groups in the molecule and from mixtures thereof.

6. The process according to claim 1, characterized in that the polyol is selected from compounds having 2 to 20 carbon atoms and from mixtures thereof.

7. The process according to claim 1, characterized in that the polyol component comprises aliphatic and/or cycloaliphatic compounds.

8. The process according to claim 1, characterized in that the polyol component comprises compounds having a molecular weight of from 62 to 182.

9. The process according to claim 1, characterized in that the polyol is selected from ethane diol, 1,2- and 1,3-propane diol, 1,2-, 1,3-, 1,4- and 2,3-butane diol, pinacol, glycerol, trimethylol methane, trimethylol ethane, trimethylol propane, erythritol, pentaerythritol, di- and polypentaerythritols, pentitols, hexitols, inositols, 1,4-dimethylol benzene, 2,4-dimethylol- 1,3-dihydroxy benzene, dihydroxy benzenes and mixtures of two or more of said compounds.

10. The process according to claim 1, characterized by choosing a B/P atomic ratio in the range of from 9/1 to 1/9.

11. The process according to claim 1, characterized by choosing a molar ratio of polyols to the total of boron and phosphorus compounds present of not higher than 3/1.

12. The process according to claim 1, characterized in that at least 2 molar equivalents of polyol are used per mole of phosphorus compound plus boron compound.

13. The process according to claim 1, characterized in that the reactants are used in aqueous solution.

14. The process according to claim 13, characterized in that the water content of the aqueous solution initially is in the range of from 15 to 55% by weight.

15. The process according to claim 13, characterized in that the reaction is conducted at a temperature of from 90° to 130° C.

16. The process according to claim 1, characterized in that reaction is conducted under reduced pressure.

17. The process according to claim 13, characterized in that reaction is conducted under reduced pressure.

18. The process according to claim 13, characterized in that reaction is conducted at a pressure of from 20 to 60 mbar.

19. The process according to any one of claims 13, 16 and 17, characterized in that reaction is conducted under thin-film vaporization of the solvent water and the reaction water.

20. The process according to any one of claims 1, 13, 16 and 17, characterized by being conducted continuously.

21. The process according to claim 1, characterized in that the polyol is selected from compounds having 2 to 6 OH-groups in the molecule and from mixture thereof.

22. The process according to claim 1, characterized in that the polyol is selected from compounds having 2 to 6 carbon atoms and from mixtures thereof.

23. The process according to claim 1, characterized by choosing a B/P atomic ratio in the range of from 7/3 to 3/7.

24. The process according to claim 1, characterized by choosing a molar ratio of polyols to the total of boron and phosphorus compounds present of not higher than 2/1.

25. The process according to claim 1, characterized in that at least 3 molar equivalents of polyol are used per mole of phosphorus compound plus boron compound.

26. The process according to claim 13, characterized in that the water content of the aqueous solution initially is in the range of from 20 to 40% by weight.

27. The process according to claim 13, characterized in that the reaction is conducted at a temperature of from 95° to 125° C.

* * * * *